(12) United States Patent
Daignault et al.

(10) Patent No.: US 10,292,761 B2
(45) Date of Patent: May 21, 2019

(54) RESECTION LOOP FOR TISSUE RESECTION AND RELATED METHOD OF USE

(71) Applicant: BOSTON SCIENTIFIC SCIMED, INC., Maple Grove, MN (US)

(72) Inventors: Kenneth J. Daignault, Holden, MA (US); Kevin Newell, Jefferson, MA (US); Ronald Ciulla, Westford, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 632 days.

(21) Appl. No.: 13/914,915

(22) Filed: Jun. 11, 2013

(65) Prior Publication Data

US 2013/0338667 A1     Dec. 19, 2013

Related U.S. Application Data

(60) Provisional application No. 61/659,181, filed on Jun. 13, 2012.

(51) Int. Cl.
| | |
|---|---|
| *A61B 18/14* | (2006.01) |
| *A61B 18/00* | (2006.01) |
| *A61B 18/12* | (2006.01) |
| *A61B 90/00* | (2016.01) |

(52) U.S. Cl.
CPC ........ *A61B 18/1485* (2013.01); *A61B 18/149* (2013.01); *A61B 2018/00547* (2013.01); *A61B 2018/00601* (2013.01); *A61B 2018/00625* (2013.01); *A61B 2018/126* (2013.01); *A61B 2018/144* (2013.01); *A61B 2018/1407* (2013.01); *A61B 2018/1417* (2013.01); *A61B 2018/1467* (2013.01); *A61B 2018/1475* (2013.01); *A61B 2090/3966* (2016.02)

(58) Field of Classification Search
CPC ...... A61B 2018/1407; A61B 2018/141; A61B 2017/00358; A61B 17/32056
USPC ....................................... 606/39–40, 47, 110
See application file for complete search history.

(56) References Cited

U.S. PATENT DOCUMENTS

| | | | |
|---|---|---|---|
| 5,197,964 A * | 3/1993 | Parins | 606/48 |
| 5,658,280 A | 8/1997 | Issa | |
| 5,766,215 A | 6/1998 | Muri et al. | |
| 6,030,383 A | 2/2000 | Benderev | |
| 6,454,727 B1 * | 9/2002 | Burbank et al. | 600/567 |
| 6,517,550 B1 * | 2/2003 | Konya | A61B 17/221 606/113 |
| 2003/0144661 A1 * | 7/2003 | Brommersma | A61B 18/149 606/46 |
| 2005/0171566 A1 * | 8/2005 | Kanamaru | A61B 17/22 606/159 |
| 2005/0245927 A1 | 11/2005 | Snay et al. | |
| 2005/0251134 A1 * | 11/2005 | Woloszko | A61B 18/149 606/46 |

(Continued)

*Primary Examiner* — Jaymi E Della
(74) *Attorney, Agent, or Firm* — Bookoff McAndrews, PLLC

(57) ABSTRACT

A medical device includes a sheath extending from a proximal end to a distal end and having a lumen extending therethrough and an end-effector disposed at the distal end of the sheath including a first resection loop configured to resect tissue and a secondary tool including one of a second resection loop and a tissue-vaporizing structure mounted distally to the first resection loop.

20 Claims, 7 Drawing Sheets

(56) References Cited

U.S. PATENT DOCUMENTS

| | | | |
|---|---|---|---|
| 2007/0060920 A1* | 3/2007 | Weitzner | A61B 18/14 606/39 |
| 2007/0185511 A1* | 8/2007 | Minosawa | A61B 17/32056 606/170 |
| 2010/0036312 A1* | 2/2010 | Krolik | A61B 17/221 604/22 |
| 2013/0006262 A1* | 1/2013 | Lampropoulos | A61B 17/221 606/113 |

* cited by examiner

RESECTION LOOP FOR TISSUE RESECTION AND RELATED METHOD OF USE

PRIORITY CLAIM

The present application claims priority to U.S. Provisional Application Ser. No. 61/659,181 entitled "Resection Loop For Tissue Resection And Related Method Of Use" filed on Jun. 13, 2012, the entire disclosure of which is incorporated herewith by reference.

FIELD OF THE INVENTION

Embodiments of the present disclosure relate generally to medical devices suitable for use in surgical procedures. In particular, embodiments of the disclosure relate to minimally invasive medical devices employed for body tissue manipulation.

BACKGROUND OF THE INVENTION

Minimally invasive medical procedures are commonly used for treating patients in an out-patient procedure and include cutting various organ layers to perform a variety of medical procedures.

One such technique, known as a transurethral resectioning of the prostate (TURP), is performed to treat benign or cancerous prostatic hyperplasia. Transurethral resection may also be performed in the bladder (TURB). It is performed by visualizing the prostate through the urethra, and removing tissue by electro-cautery or sharp dissection, which is inserted into the urethra through a resectoscope. An electric current heats the tissue sufficiently to break intercellular bonds, cutting the tissue into strips, which gets removed from the body through the resectoscope. An electric current may also be used to vaporize the tissue to aid in removal of the tissue strips.

Extensive bleeding can occur because of the resection, which can obstruct the resectoscope to dangerous blood loss levels. Additionally, veins have a negative pressure and may take up ambient fluid when cut, causing further complications. In addition, the resection procedure may develop symptoms of urinary incontinence in some patients.

Therefore, there exists a need for an improved procedure for the transurethral resectioning of the prostate, which reduces the blood loss and eliminates any inconvenience caused after the procedure.

SUMMARY OF THE INVENTION

In accordance with one embodiment, provided a medical device that includes a sheath with a proximal end and a distal end, and a lumen extending from the proximal end to the distal end is provided. The medical device includes an end effector disposed at or extendable from the distal end of the sheath. The end effector includes a first resection loop and a secondary tool in the form of a second resection loop or a tissue-vaporizing structure mounted distally to the first resection loop. The first resection loop and secondary tool may be implemented as a pair of bipolar electrodes. In the case where the end effector includes a second resection loop, the second loop may be configured for deeper cuts than the first resection loop. The tissue-vaporizing structure may include a tissue-vaporizing button or a tissue-vaporizing loop.

Still further, according to the disclosure, provided a method for manipulating tissue within the body of a patient is provided, the method comprising: advancing a medical device into the body, the medical device comprising: a sheath having a proximal end, a distal end, and a lumen extending between the proximal and distal ends; an end-effector disposed at or extendable from the distal end of the sheath, the end-effector including a first resection loop configured to resect tissue, and a secondary tool that includes at least one of a second resection loop and a tissue-vaporizing structure, mounted distally relative to the first resection loop, the method further comprising actuating the first resection loop and the secondary tool, and retracting the end-effector or the entire medical device while engaging the tissue with the end effector. The secondary tool may include a second resection loop configured for deeper cuts. The secondary tool may be a tissue-vaporizing tool configured to vaporize tissue, the method comprising resecting a section of tissue and vaporizing the resected tissue. The tissue vaporizing tool may instead be implemented as a button, ball or wire loop structure.

Additional objects and advantages of the present disclosure will be set forth in part in the description, which follows, and in part will be obvious from the description, or may be learned by practice of the claimed disclosure. The objects and advantages of the present disclosure will be realized and attained by means of the elements and combinations particularly pointed out in the appended claims.

It may be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

DESCRIPTION OF THE EMBODIMENTS

Reference will now be made in detail to embodiments of the present disclosure, examples of which are illustrated in the accompanying drawings. Wherever possible, the same reference numbers will be used throughout the drawings to refer to the same or like parts. The term "distal" refers to the end farthest away from a medical professional when introducing a device in a patient. By contrast, "proximal" refers to the end closest to the medical professional when placing a device inside the patient.

Embodiments related to the present disclosure are directed to medical devices for minimally invasive surgical procedures, mainly, transurethral resectioning of the prostate (TURP). The medical devices include resection loops for cutting tissue inside the body. Conventional resection procedures involve retraction of the resected tissue after cutting. The medical device disclosed as one aspect of this disclosure not only performs cutting, but also eliminates the exercised tissue by vaporizing it.

In the following sections, embodiments of the present disclosure will be described using an exemplary body organ—the prostate for the transurethral resectioning (TURP). It will be understood that this choice is merely exemplary and that the device may be utilized in any other suitable organ, such as the colon, duodenum, stomach, esophagus, bladder, uterus, or any other organ that may be subject to polyps, lesions, stones, and the like. Further, the medical device may be employed with other known surgical tools without departing from the scope of the present disclosure. As those skilled in the art will understand, the exemplary device according to the invention may be configured to fit any standard resectoscope used in TURP procedures. Likewise, for other types of tissue resection procedures, embodiments are contemplated that operate through any type of endoscope, sheath, cannula or catheter.

Figure 1:
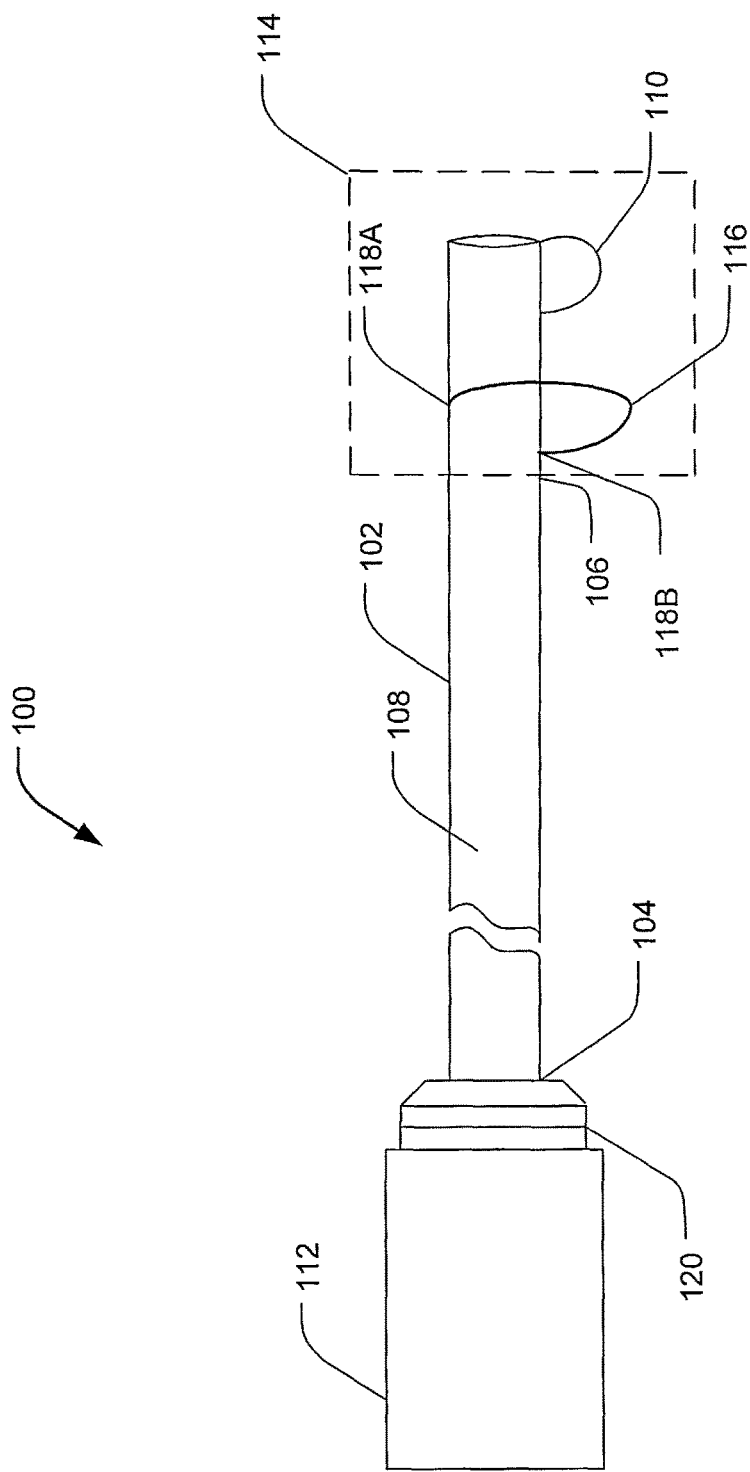
FIG. 1 illustrates an exemplary medical device according to embodiments of the present disclosure.

FIG. 1 illustrates an exemplary medical device 100 according to one embodiment of the present disclosure. The device 100 includes an elongate sheath 102 having a proximal end 104, a distal end 106, and a lumen 108 extending between the proximal and distal ends 104 and 106. The proximal end 104 of the elongate sheath 102 is connected to a handle 112, while the distal end 106 is connected to an end-effector 114. The end effector 114 includes a resection mechanism and a tissue elimination mechanism. The resection mechanism includes a resection loop 116 for resecting the target tissue, while the tissue elimination mechanism includes a tissue-vaporizing structure 110 for vaporizing tissue resected by the resection loop 116. As those skilled in the art will understand, the tissue-vaporizing structure 110 may vaporize a portion of tissue located adjacent a target tissue site, the vaporization aiding in separation of the target tissue from the body. In one embodiment, the separated tissue may subsequently be withdrawn from the body through the sheath 102.

Sheath 102 may be any known endoscopic device used for resectoscopy, colonoscopy, cholangioscopy, or mucosal resection. In the embodiments of the present disclosure, sheath 102 may be a resectoscope, adapted to advance into a urethral cavity for performing transurethral resection of the prostrate.

The sheath 102 may have a substantially circular cross-section. Other suitable cross-sectional shapes, such as elliptical, oval, polygonal, or irregular are also contemplated. The sheath 102 may be made from any of a group of suitable biocompatible materials such as metals, polyurethane, plastics, etc. Moreover, sheath 102 is preferably flexible along its length so that it may be bent along any path over which the endoscope is bent as it travels through the body. It may also be provided with adaptations for flexure along its length. Alternatively, the sheath's distal end 106 may be flexible while proximal portions thereof remain substantially rigid. The sheath 102 may be substantially flexible to permit movement thereof through tortuous paths in the body while maintaining a column strength sufficient to enable the device 100 to be pushed forward in the body. Moreover, the distal end 106 may be steerable, allowing an operator to accurately position the sheath 102 within the body. Steering mechanisms, such as mechanical or electrical actuators known in the art may be provided on the handle 112 to aid in insertion.

The sheath 102 may include suitable coatings. For example, a lubricious coating may be applied to an outer surface of the sheath 102 to facilitate insertion into a body lumen or an endoscopic device. The outer surface of the sheath 102 may also include radiopaque markings to aid in detecting a position thereof within the body. As those skilled in the art will understand, the radiopaque markings are adapted to produce a relatively bright image on a fluoroscopic monitor or other imaging device. Suitable radiopaque materials may be selected from a group of materials including gold, palladium, platinum, tantalum, tungsten alloy, or polymeric materials loaded with radiopaque agents such as barium sulfate ($BaSO_4$) or bismuth sub-carbonate (($BiO)_2$ $CO_3$). The sheath 102 may further be coated with an antibacterial coating to inhibit bacterial growth on the outer surface. The antibacterial coating may contain an inorganic antibiotic agent, disposed in a polymeric matrix that adheres the antibiotic agent to the outer surface.

The lumen 108 may have one or more working channels (not shown) extending from the proximal end 104 to the distal end 106. Operators may insert different medical tools within one or more of the working channels. For example, an operator may place a cutting tool in one channel and a retraction or a vaporization tool in the other. Additionally, during the procedure, the operator may insert a light source, a camera, an injector, or a cauterization tool within the one or more channels of the sheath 102. It may be understood that other exemplary tools may also be inserted in the working channels without departing from the present disclosure.

The handle 112 allows an operator to grip the medical device 100 for manipulation within the body. In order to provide a better grip, an outer surface of the handle 112 may include grooves or other patterning. The handle 112 may further comprise portions with softer and/or tackier material. The handle 112 includes ports (not shown) for inserting tools into the working channels (not shown) of the sheath 102. In addition, the handle 112 may also include the steering mechanism (not shown) to aid in navigation of the distal end 106 through the body. The steering mechanism (not shown) may include mechanical levers, sliders, pulleys, dials, electronic buttons, switches, joysticks or any other combination of mechanical or electronic controls. The sheath steering means are widely known in the art and any means may be utilized without departing from the scope of the present disclosure. The handle 112 may also include mechanisms to actuate the end-effector 114.

The resection loop 116 is a cutting tool adapted to resect tissue. As shown, the resection loop 116 may be a circular ring-like structure, having its first and second ends connected to the outer surface of the sheath 102. Other suitable shapes may be contemplated such as "U" shape, "V" shape, semicircular, semi-elliptical, square, rectangular, wavy, zig-zag, etc. Specifically, the shape of the loop may be selected to increase a contacting surface area with the tissue, thus aiding in cauterization. Furthermore, although the loop 116 is depicted with a two-dimensional curvature, any plurality of three-dimensional bends may also be incorporated therein without deviating from the scope of the invention. The bends of the loop 116 may also include any number of pointed corners. The sheath's outer surface may include slots 118A and 118B for connecting the resection loop 116 to the sheath 102. The slots 118A, 118B may be provided in any position along the outer surface and may be separated from one another along a circumference of the sheath 102 by any distance without deviating from the scope of the invention. As those skilled in the art will understand, the position of the slots 118A, 118B may be selected to impart a desired shape and size to the resection loop 116 and to conform to the requirements of a particular procedure. In one embodiment, resection loop 116 may be permanently connected to the sheath 102. Alternatively, resection loop 116 may form part of a tool that may be slidably disposed within the working channel of the sheath 102 and, in an operative configuration, is extendable distally out of the distal end 106 to assume the desired shape.

Dimensions of the resection loop 116 may vary based on the intended use and application. The resection loop 116 may have a uniform thickness throughout. Alternatively, first and second ends of the resection loop 116 may be thinner while a center portion thereof may be thicker, and vise versa. In addition, a diameter of the resection loop 116 may be suitably chosen based on the thickness of tissue to be resected. The resection loop 116 wire may have any cross-sectional geometry including round, square, rectangular, semicircular, etc. The resection loop 116 may further include a roughened surface or focal points to aid in grasping tissue.

The suitable materials for making the resection loop 116 may be selected from a group of materials including, but not limited to, high carbon steel, ceramics, plain carbon, cast alloys using alloying elements such as manganese, chromium, tungsten, vanadium, molybdenum, cobalt, and niobium. In some embodiments, tungsten carbide may also be employed.

The resection loop 116 is connected to an electric source connected to one of the proximal end 104 of the sheath 102 and the handle 112. This source provides the required electric current through the loop to facilitate the cutting process. For instance, the power source may be a radio frequency (RF) power supply providing, for example, a 350 kHz signal at 100 to 300 W. An electric current heats the resection loop 116 sufficiently to permit heating of the tissue to a temperature sufficient to break the intercellular bonds (present within the tissue), cutting the tissue into strips or chips. In accordance with one embodiment of the disclosure, these strips or chips are then vaporized by the tissue-vaporizing structure 110, which follows the resection loop 116 as the device 100 is slowly withdrawn proximally. In an embodiment, in which the end effector is slidably disposed within the sheath 102, proximal movement of the end-effector 114 can be achieved by retracting the end-effector 114 into the sheath 102. The resection loop 116 may be coated with insulation at various points. In another embodiment, the coating (not shown) may aid in resectioning.

In one embodiment of the present disclosure, the tissue-vaporizing structure 110 is a substantially semi-circular button or ball electrode. It is noted, however, that the tissue-vaporizing structure 110 may be formed in any shape including, but not limited to, a rectangle, trapezoid, ball, dome, barrel, sphere, wheel, block or irregular shape without deviating from the scope of the invention. With any vaporizing structure 110 configuration, it may be desired that a cross-sectional area of the tissue-vaporizing structure 110 is sufficiently large to coagulate a substantially large target tissue area. Consequently, rectangular, square, trapezoidal or any configuration with a substantially flat area of contact with the tissue may be desirable. It will be appreciated that with the increased surface area, in order to maintain sufficiently high current at the tissue-vaporizing structure 110 to vaporize tissue the power supply must provide the required power. In the case of a bipolar electrode in which the resection loop and vaporizing structure form the two electrodes, the sizes and thicknesses of the electrodes are chosen to achieve a cutting function at the resection loop and a vaporizing function at the vaporizing structure.

The materials used for making the tissue-vaporizing structure 110, may be selected from a group of materials, including but not limited to, high carbon steel, ceramics and carbon, cast alloys using alloying elements such as manganese, chromium, tungsten, vanadium, molybdenum, cobalt, and niobium. In addition, wire leads extending along the surface of the sheath 102 or within a channel of the sheath may be used for connecting the resection loop 116 and the tissue-vaporizing structure 110 to a power source, for its activation. These energy sources may be placed at the proximal end of the sheath 102 or on the handle 112. The tissue vaporizing structure 110 may include a coating to, for example, prevent the tissue from sticking thereto.

The present disclosure facilitates resection along with vaporization of the resected tissue. Both the resection and vaporizing structure function together for efficient elimination of the tissue from the target region. The resection loop 116 cuts the tissue, while the tissue-vaporizing structure 110 vaporizes the tissue.

Figure 2A:
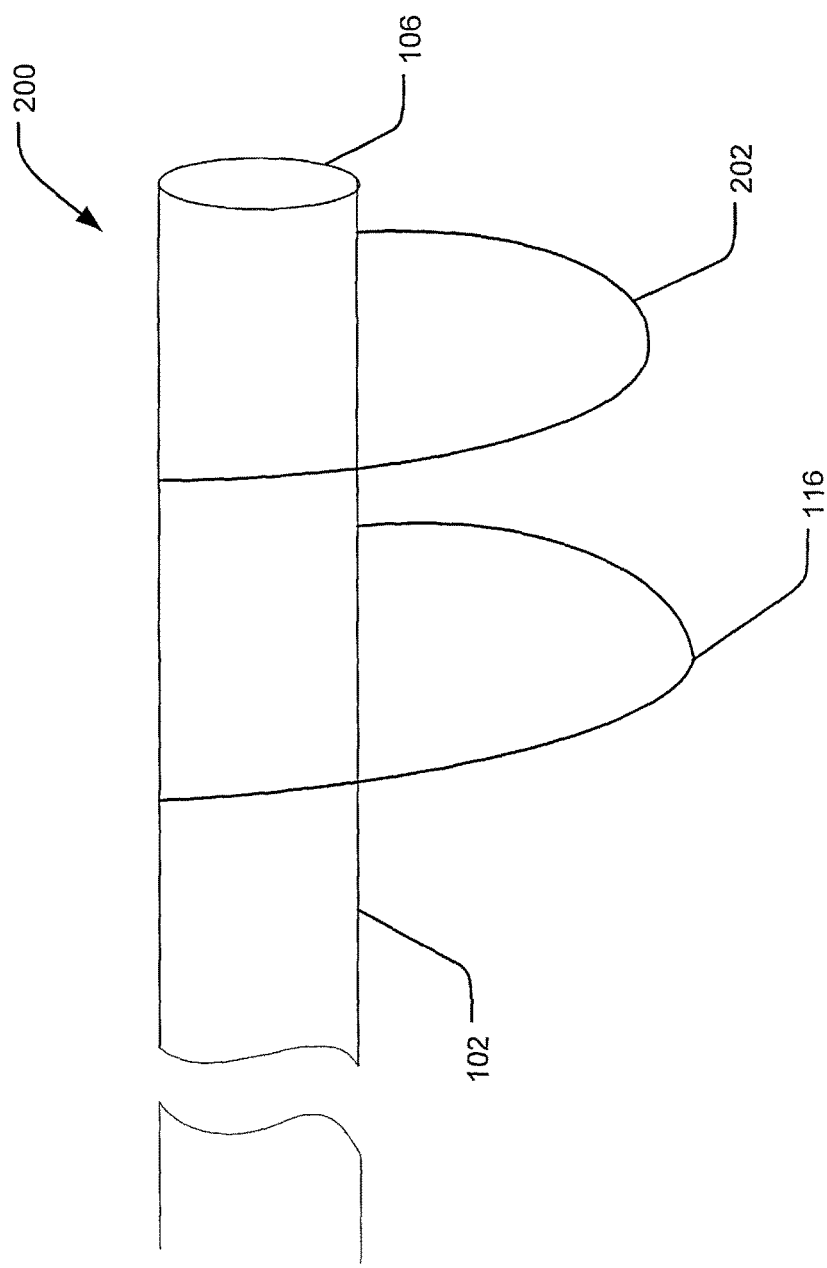
FIGS. 2A and 2B, illustrate one embodiment of the distal end of an exemplary medical device of the disclosure.
Figure 2B:
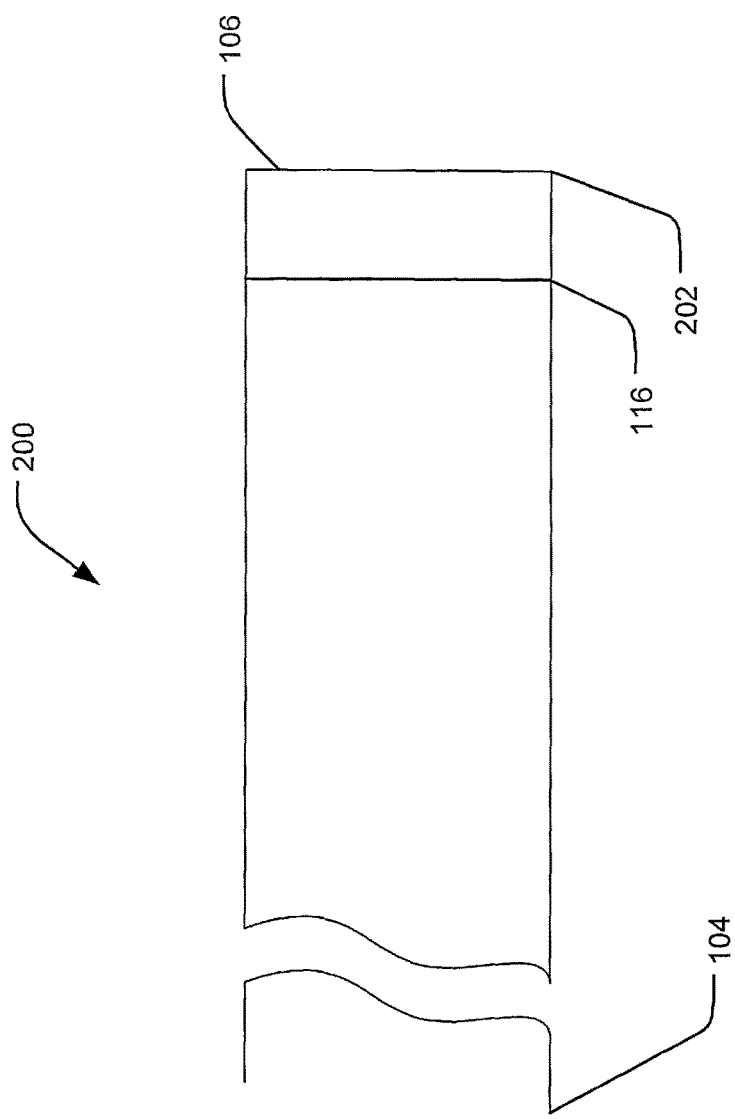

FIGS. 2A and 2B illustrate the distal end of another embodiment of an exemplary medical device 200, which sets out a double loop design. The medical device 200 includes many components similar to those shown in device 100, such as sheath 102, lumen 108, and resection loop 116. In addition, the medical device 200 includes a second resection loop 202 positioned distally from the resection loop 116 at a suitable distance. The second resection loop 202 may have a different cross-sectional profile than the resection loop 116. For example, the resection loop 116 may be formed with a substantially circular cross-section while the second resection loop 202 may be formed with a substantially triangular cross-section.

The resection loop 202 may be similar in design and functionality to the resection loop 116. In some embodiments, however, the dimensions and configuration of the resection loops 116, 202 may vary. For example, loop 116 may be circular, while loop 202 may be V-shaped for providing varying resection depths. In addition, a diameter of loop 202 may be larger than a diameter of the loop 116, as shown in FIG. 2A. It may be noted that these dimensions are exemplary only and that any other dimensions may be used without deviating from the scope of the invention. Furthermore, the loop 202 may have any shape, including wavy, zig-zag, etc.

The double loop design of the device 200 facilitates resecting two sections of a tissue in a single pass. An axial length between the resection loops 116, 202 may be selected to conform to a size of tissue to be resected, wherein a greater length between the loops 116, 202 may correspond to a greater dimension of the tissue to be resected. In one embodiment, the resection loops 116, 202 may be connected to form one electrode of a bipolar electrode arrangement with a return electrode (not shown) being separated axially along the sheath 102 from the resection loops 116, 202. In another embodiment, the two resection loops 116, 202 may be connected to a power supply (not shown) to define the two electrodes of a bipolar arrangement, as those skilled in the art will understand. Further it may be noted that device 200 may also include the tissue-vaporizing structure 110 provided on the distal end 106 without deviating from the scope of the invention.

Figure 2C:
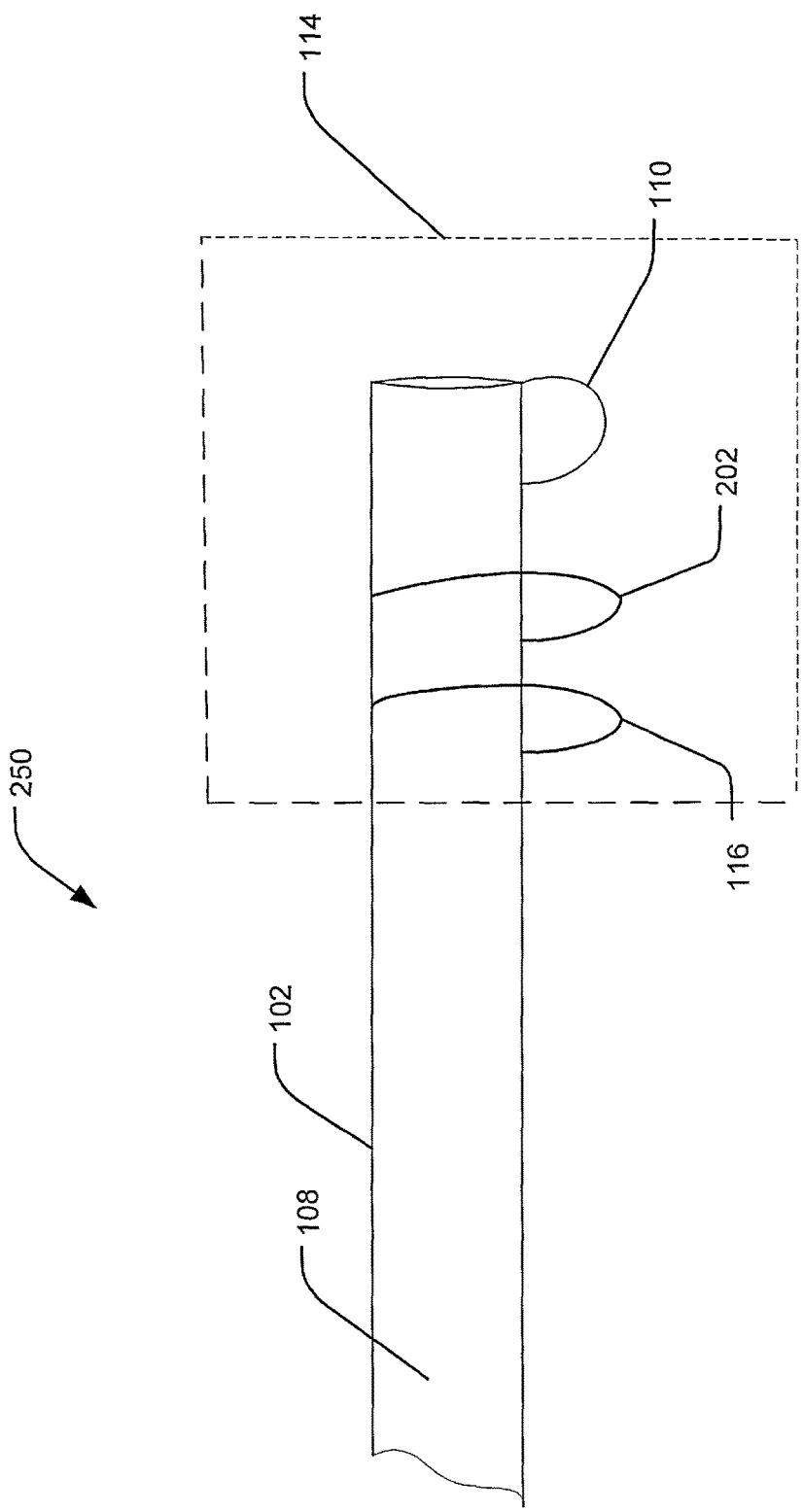
FIG. 2C illustrates the distal end of another embodiment of an exemplary medical device of the disclosure.

FIG. 2C depicts a bipolar device 200 according to another embodiment of the invention. The device 200 is formed substantially similar to the device 200 but comprises the tissue-vaporizing structure 110 on the distal end 106. In one embodiment of present disclosure, both the resection loops 116, 202 and the tissue-vaporizing structure 110 may be activated simultaneously. As those skilled in the art will understand, the bipolar device 200 of FIG. 2C may applies an electric current between the loops 116, 202 so that a portion of tissue positioned therebetween is vaporized. Typically, the resection loops 116, 202 will cause resected tissue to be lifted away from the underlying tissue mass allowing the tissue-vaporizing structure 110 to easily vaporize the lifted, resected tissue. The diameter of at least one of the resection loops 116 or 202 suspending from the sheath 102 may be greater than the height of the vaporizing structure 110. This allows the loops 116, 202 to resection and/or contact the tissue for resection without the vaporizing structure 110 touching the underlying body of tissue.

Figure 3:
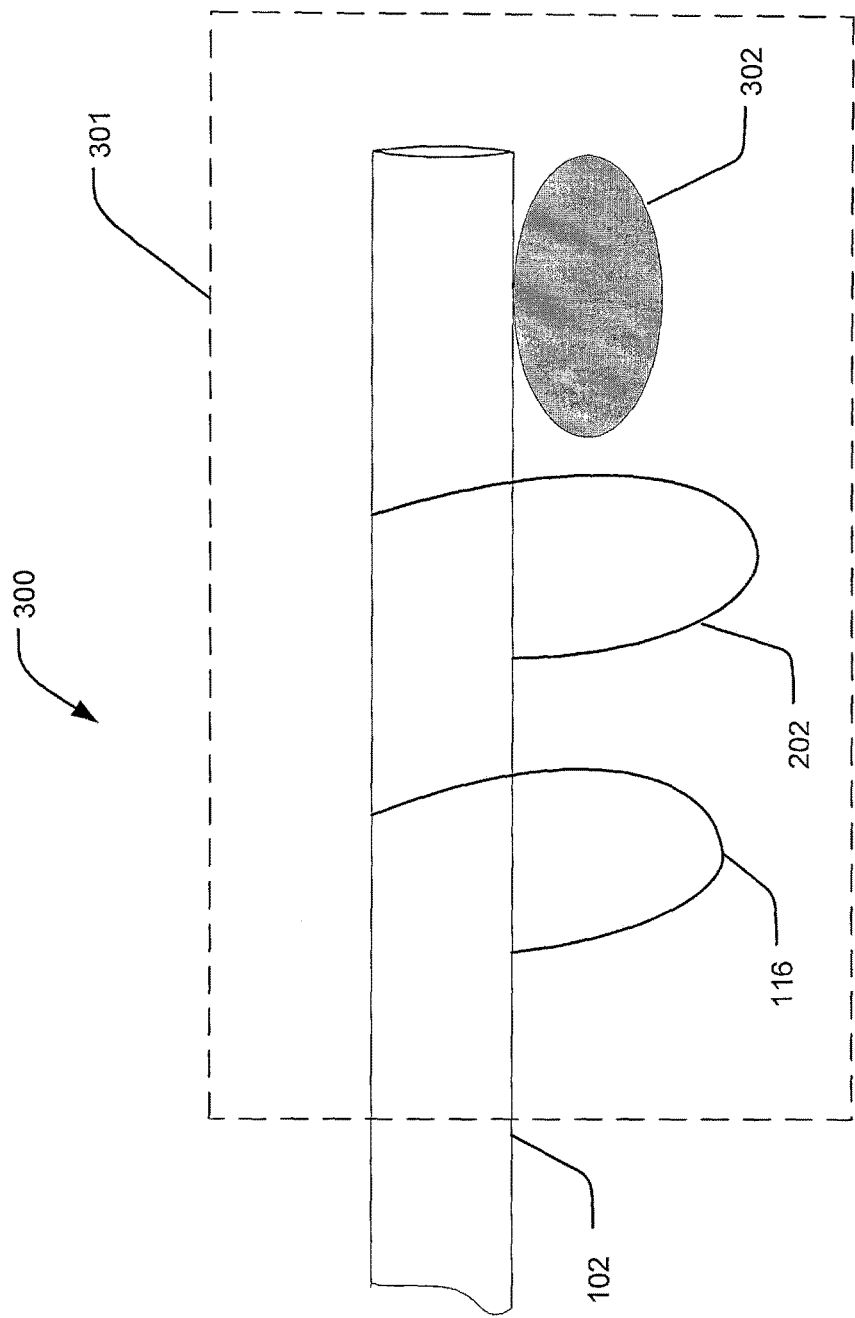
FIG. 3 illustrates the distal end of yet another embodiment of an exemplary medical device of the disclosure.

FIG. 3 illustrates the distal end of an exemplary medical device 300 depicting an end-effector 301. The medical device 300 includes many components that are similar to those shown in device 200, such as resection loops 116, 202, and a vaporizing structure 302 in the form of a ball tip positioned distally to the resection loops 116, 202. However, in this embodiment the resection loops 116, 202 and vaporizing structure 110 are implemented as tools extendable from the sheath 102 instead of being secured to the distal end of the sheath 102. In another embodiment of the invention (now shown), the sheath 102 may comprise an enlarged diameter portion at a distal end thereof configured to aid in capturing and housing larger tissue chips from the body (e.g., a portion of tissue that is not vaporized). Furthermore the enlarged diameter portion facilitates in insertion of the tools through the sheath 102.

A ball tip 302 may be provided over a distal portion of the sheath 102, the ball tip 302 being substantially spherically shaped and adapted to cauterize tissue. The ball tip 302 may be welded to the sheath 102. It is noted however, that alternate attachment means are also envisioned. Other suitable shapes such as oval, ring, cube, cuboid, or other irregular shapes may also be implemented. It should be evident that dimensions of the ball tip 302 may vary based on the intended use and application. In addition, the ball tip 302 may be flexible, rigid, or a semi-rigid structure. For example, ball tip 302 may be configured as a bipolar structure with one or both of the resection loops 116, 202 dimensioned to produce a current density in the tissue adjacent the ball tip 302 that may be sufficient to vaporize the tissue.

The present disclosure provides for a method of resecting tissue and subsequently vaporizing the resected tissue. Both the resection and vaporizing mechanisms function together for efficient elimination of the tissue from the target region. The resection loops 202, 116 cut the tissue, while the ball tip 302 vaporizes the tissue by burning and searing as tissue gets cut by the resection loops. The resection loops 116 and 202 may be configured to deflect the resected tissue toward the vaporizing ball tip 302, which scallops upward toward the ball tip 302, and is then directly vaporized.

Figure 4A:
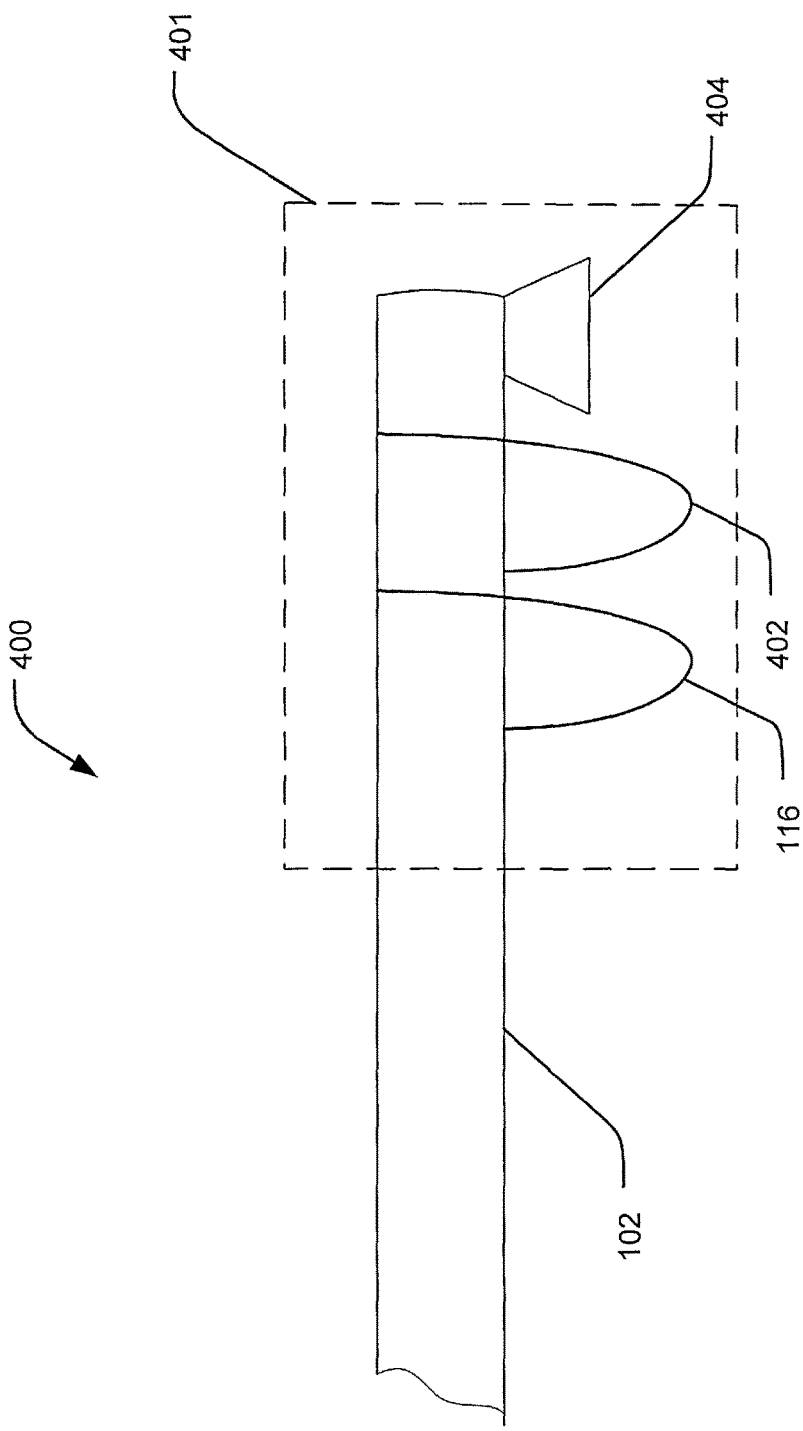
FIG. 4A illustrates the distal end of yet another embodiment of an exemplary medical device of the disclosure.
Figure 4B:
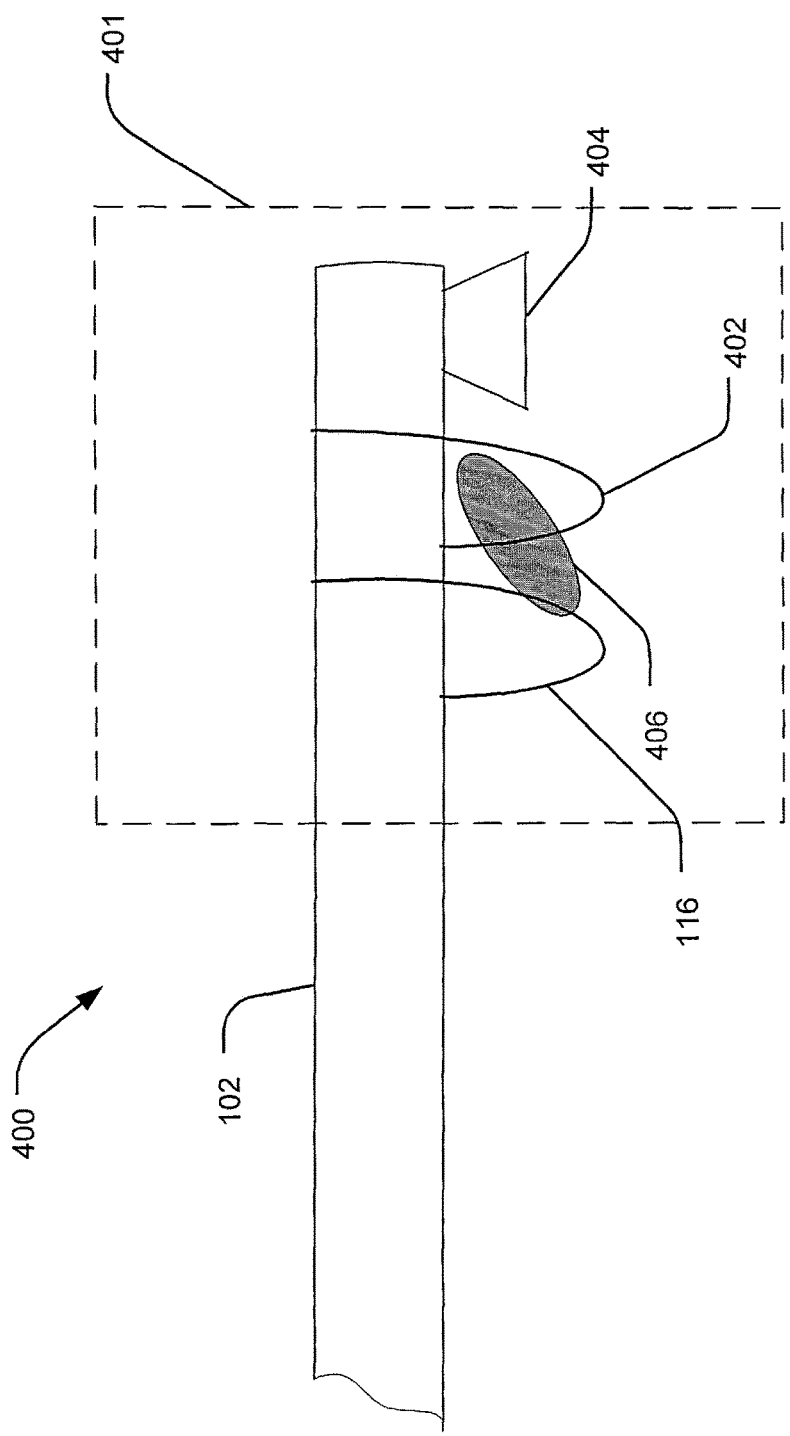
FIG. 4B illustrates the distal end of yet another embodiment of an exemplary medical device of the disclosure.

FIGS. 4A and 4B illustrate another embodiment of the present disclosure comprising an exemplary medical device 400 with an end-effector 401. The end-effector 401 is similar to the end-effector of medical device 200 (FIG. 2A) having a double loop design, which includes the resection loop 116 and a vaporization loop 402. The vaporization loop 402 is placed distally to the resection loop 116. The vaporization loop 402 may be similar in dimension and configuration to the resection loop 116, as shown. Alternatively, the two loops may differ from each other. For example, the vaporization loop 402 may have a greater diameter than the loop 116.

In general, the loops 116 and 402 are configured to perform two functionalities—resection and vaporization. In the illustrated embodiment, the loop 402 is provided with both cutting and vaporizing functionalities. Different arrangements of the resection and vaporization loop may be contemplated. In one embodiment, the vaporization loop 402 may or may not perform vaporization. Alternatively, the vaporization loop 402 may be configured to resect, while the resection loop 116 performs both resection and vaporization. In some embodiments, both the loops 116, 402 may perform resection and vaporization individually.

For cutting purposes, the loops 116, 402 operate in a similar fashion as already described with respect to FIG. 1. For vaporization, however, the vaporization loop is provided with higher electric current that vaporizes the tissue. To this end, the loops 116, 402 may be bipolar structures to perform the resection and vaporizing. However, other mechanisms may be employed for resecting and for vaporization including, but not limited to, RF mono-polar ablation, etc.

The end-effector 401 includes a button 404 permanently attached to the sheath 102 and configured to initiate the vaporization capabilities of the loops. The button 404 is placed close to the distal tip of the sheath 102 and may be configured to assume any desired shape including, but not limited to trapezoidal, square, and spherical. A height of the button 404 is smaller than the diameter of the loops 116, 402. In an operative configuration, the button 404 may be actuated by an actuator (not shown) provided on the handle (not shown) at the proximal end of the medical device 400. For example, the handle may include knobs, buttons, a touch screen control or other similar devices to move the button 404 between an on and an off state to control a vaporization of adjacent tissue. In one exemplary embodiment, the actuator may be connected to the button 404 using conductive wires extending along the length of the sheath 102. As described in greater detail in earlier embodiments, any portion of the button 404 may include a coating serving as, for example, an insulator.

In each of the embodiments discussed above, the retraction of the loops around a portion tissue 406 performs resection followed by vaporization (as shown in FIG. 4B). For example, a first pass of retracting of the loop could be conducted in order to resect the tissue 406, and thereafter a second pass could be performed to vaporize the resected tissue 406. In one embodiment of the present disclosure, the vaporization loop 402 may be adapted to perform the vaporization of the tissue 406 resected by the resection loop 116, thereby allowing both resection and vaporization to be performed in one pass.

During the procedure, a surgeon may be able to control the cutting and vaporization structures. The actuation mechanism (not shown) may be used to activate the resection loop 116 and the vaporization loop 402. Alternatively, as the resection loop 116 starts cutting the tissue, a section of the loop 116 advances into the tissue, causing the button 404 to contact a body part and triggering the activation of the vaporization loop 402. It will be appreciated that if the two loops act as bipolar electrodes (one electrode acting as the return path for the first) their activation would by necessity be simultaneous.

Various alternatives of the medical device, described in connection with FIGS. 1-4B, may be contemplated. For example, at least one of the resection loops 116, 202 or the vaporizing structure 110, 302, 402 may remain collapsed within the sheath 102 during insertion or retrieval. Once the tools are deployed, they may extend to assume their desired shapes. In addition, the resection mechanisms and the removal mechanisms may be used in combination. For example, the medical device may include a double loop design with the vaporizing structure 110 or 302. In other cases, the medical device may include the resection loop 116, having vaporization capabilities, along with a second vaporizing structure, for example, in the form of a ball or button. In addition, the number of resection loops provided may vary, as desired.

In addition, the medical devices may be constructed in many forms, mainly as electro-surgical devices that are used in transurethral resectioning of the prostate (TURP). The devices may also be configured to resect the lining of the uterus (endometrioma) or for use in transurethral resectioning of the bladder (TURB). The device may also serve its application in other fields, including laparoscopic and cystoscopic procedures.

The following sections describe a method of using the medical device 200 (FIG. 2C) for performing a transurethral resection procedure for removing an enlarged portion of the prostate, where the end-effector is implemented as tools retractable into a sheath. The devices may also be employed to perform various other procedures including endoscopy, laparoscopy, cystoscopy, removing tumors from body parts such as esophagus, cervix, or uterus, or to resect the lining of the uterus, and other resection procedures such as in endoscopic mucosal resection procedures.

For resection, the patient is prepared by inserting the medical device 200 through the urethra toward the prostate. In some embodiments, the physician may first inspect the region using a visualization device inserted through the sheath 102. In addition, the target region may then be flushed with some liquid, such as distilled water or glycine.

Once the sheath 102 is appropriately deployed, the resection loops 116, 202 and the elimination mechanism such as the vaporizing structure 110 are actuated by applying a proximally directed pressure to an actuation mechanism (not shown) on the handle 112, forcing the resection loops 116, 202 radially outward and into contact with the target tissue Power is then supplied to the resection loops 116 and 202, by turning on the electrical source (not shown), causing current to flow through the tissue between the resection loops 116, 202 and the tissue-vaporizing structure 110. At any time during the operation, the physician may manipulate the actuation mechanism (not shown) to cause the resection loops 116, 202 to contract into the sheath 102 or expand further radially to conform to the requirements of the procedure. Once the target resection procedure has been performed, the physician may release the proximally directed pressure applied on the handle and permit the resection loops 116, 202 to retract back toward the sheath 102.

Other embodiments of the present disclosure will be apparent to those skilled in the art from consideration of the specification and practice of the embodiments disclosed herein. It is intended that the specification and examples be considered as exemplary only, with a true scope and spirit of the disclosure being defined by the following claims.

What is claimed is:

1. A medical device, comprising:
   a sheath extending from a proximal end to a distal end and having a lumen extending therethrough, wherein the sheath extends along a longitudinal sheath axis; and
   an end-effector disposed at the distal end of the sheath including:
   a first resection loop having a fully expanded configuration;
   a second resection loop mounted distally of the first resection loop and having a fully expanded configuration, wherein each of the first resection loop and the second resection loop is individually expandable to its fully expanded configuration radially outwardly from an outer wall of the sheath relative to the longitudinal sheath axis; and
   a tissue vaporizer mounted to the outer wall of the sheath distally of the second resection loop, wherein the tissue vaporizer is a button electrode;
   wherein, in an insertion configuration, the first resection loop is positioned against the outer wall of the sheath.

2. The medical device of claim 1, wherein the second resection loop is configured to form deeper cuts than the first resection loop.

3. The medical device of claim 1, wherein the second resection loop is a coagulation tool.

4. The medical device of claim 1, further comprising an actuator configured to control the end-effector.

5. The medical device of claim 1, wherein the first resection loop is movable between the insertion configuration and the fully expanded configuration.

6. The medical device of claim 5, wherein, in the insertion configuration, the first resection loop is positioned against the outer wall of the sheath and, in the fully expanded configuration, the first resection loop is moved outwardly from the outer wall of the sheath.

7. The medical device of claim 5, wherein the second resection loop is movable between an insertion configuration and the fully expanded configuration.

8. The medical device of claim 7, wherein, in the insertion configuration, the second resection loop is positioned against the outer wall of the sheath and, in the fully expanded configuration, the second resection loop is positioned radially outwardly of the outer wall of the sheath.

9. The medical device of claim 1, wherein the tissue vaporizer extends radially outwardly from the outer wall of the sheath relative to the longitudinal sheath axis.

10. An end-effector for a medical device, comprising:
    a first resection loop having a fully expanded configuration;
    a second resection loop mounted distally relative to the first resection loop and having a fully expanded configuration, wherein each of the first resection loop and the second resection loop is individually expandable between an insertion configuration and its fully expanded configuration relative to an end-effector longitudinal axis; and
    a button electrode mounted to a circumferential wall of the end-effector distally of the second resection loop;
    wherein the first resection loop extends from a first opening and a second opening, different than the first opening, in the circumferential wall of the end-effector.

11. The end-effector of claim 10, wherein, in the insertion configuration, each of the first resection loop and the second resection loop is positioned against the circumferential wall of the end-effector and, in the fully expanded configuration, each of the first resection loop and the second resection loop is positioned radially outwardly of the circumferential wall of the end-effector.

12. The end-effector of claim 10, wherein, in the fully expanded configuration, the second resection loop is positioned radially outwardly of the circumferential wall of the end-effector and radially outwardly of the first resection loop.

13. The end-effector of claim 12, wherein, in the fully expanded configuration, the first resection loop is positioned radially outwardly of the circumferential wall of the end-effector and radially outwardly of the button electrode.

14. The end-effector of claim 10, further comprising an actuator configured to control the end-effector.

15. The end-effector of claim 10, wherein the button electrode extends radially outwardly of the circumferential wall of the end-effector relative to the end-effector longitudinal axis.

16. An end-effector for a medical device, comprising:
a first resection loop;
a second resection loop, wherein each of the first resection loop and the second resection loop is movable between an insertion configuration and a fully expanded configuration, wherein in the fully expanded configuration, each of the first resection loop and the second resection loop extends radially outwardly from an outer wall of a sheath having a longitudinal axis; and wherein, in the fully expanded configuration, the second resection loop extends farther radially outwardly of the outer wall of the sheath than the first resection loop relative to the longitudinal axis; and an electrode extending radially outwardly from the outer wall of the sheath relative to the longitudinal axis, wherein the electrode is a button electrode coupled to the outer wall of the sheath and positioned distally of both of the first resection loop and the second resection loop;
wherein the first resection loop extends from a first opening and a second opening, different than the first opening, in the outer wall of the sheath.

17. The end-effector of claim 16, further comprising an actuator configured to control the end-effector.

18. The end-effector of claim 16, wherein the second resection loop is a coagulation tool.

19. The end-effector of claim 16, wherein at least one of the first resection loop or the second resection loop in its fully expanded configuration extends radially outwardly of the outer wall of the sheath to a greater extent than the button electrode.

20. The end-effector of claim 19, wherein both of the first resection loop in its fully expanded configuration and the second resection loop in its fully expanded configuration extend radially outwardly of the outer wall of the sheath to a greater extent than the button electrode.

* * * * *